United States Patent
Mansoor

(10) Patent No.: US 11,737,715 B1
(45) Date of Patent: *Aug. 29, 2023

(54) RADIOLOGIC BIOPSY SYSTEM AND METHOD

(71) Applicant: LILIUM CANDIDUM, LLC, Bloomfield Hills, MI (US)

(72) Inventor: Brandon Mansoor, Bloomfield Hills, MI (US)

(73) Assignee: LILIUM CANDIDUM, LLC, Bloomfield Hills, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 17/889,290

(22) Filed: Aug. 16, 2022

Related U.S. Application Data

(63) Continuation of application No. 17/699,097, filed on Mar. 19, 2022, now Pat. No. 11,457,880.

(51) Int. Cl.
*A61B 6/03* (2006.01)
*A61B 6/00* (2006.01)
(Continued)

(52) U.S. Cl.
CPC ............... *A61B 6/032* (2013.01); *A61B 6/12* (2013.01); *A61B 6/4092* (2013.01);
(Continued)

(58) Field of Classification Search
CPC ......... A61B 6/032; A61B 6/12; A61B 6/4092; A61B 6/4441; A61B 6/584; A61B 6/04
See application file for complete search history.

(56) References Cited

U.S. PATENT DOCUMENTS

| 5,339,347 A | 8/1994 | Slatkin et al. |
| 7,286,628 B2 | 10/2007 | Donnelly et al. |

(Continued)

FOREIGN PATENT DOCUMENTS

| CN | 2686535 Y | 1/2004 |
| CN | 104569002 B | 10/2013 |

(Continued)

OTHER PUBLICATIONS

Freeman, Tami, From whole-organ to cellular resolution: synchrotron X-ray images reveal COVID-19 lung damage; published on Nov. 16, 2021; 4 pages; URL: https://physicsworld.com/a/from-whole-organ-to-cellular-resolution-synchrotron-x-ray-images-reveal-covid-19-lung-damage/.

(Continued)

*Primary Examiner* — Courtney D Thomas
(74) *Attorney, Agent, or Firm* — Dean W. Amburn

(57) ABSTRACT

A method of performing a radiological biopsy and associated system includes scanning a living human subject with a CT scanner to locate coordinates of an area of potential pathology and then using the coordinates to direct synchrotron radiation to a location at, or proximate the coordinates to obtain a high-resolution image of the area of potential pathology. The CT scan is accomplished with a CT scanner such as a C-Arm, vertical or horizontal CT scanner. A synchrotron radiation source emits synchrotron radiation through the subject and is processed by a processing system. The method and system allow for concurrent or sequential scanning of the subject by the CT scanner and synchrotron radiation scanner. The resulting images provide histological resolution of areas of potential pathology.

20 Claims, 7 Drawing Sheets

(51) Int. Cl.
  *A61B 6/04*       (2006.01)
  *A61B 6/12*       (2006.01)
(52) U.S. Cl.
  CPC ............ *A61B 6/4441* (2013.01); *A61B 6/584* (2013.01); *A61B 6/04* (2013.01)

(56) References Cited

U.S. PATENT DOCUMENTS

| 7,742,564 | B2 | 6/2010 | Parham et al. | |
|---|---|---|---|---|
| 11,457,880 | B2 * | 10/2022 | Mansoor | A61B 6/032 |
| 2021/0077045 | A1 | 3/2021 | Wen | |
| 2021/0123873 | A1 | 4/2021 | Silver | |

FOREIGN PATENT DOCUMENTS

| CN | 107014841 A | 5/2017 |
|---|---|---|
| WO | WO2021108742 A1 | 6/2021 |

OTHER PUBLICATIONS

Toyaman et al., Make Life Visible by Toyama et al, published in 2020; 285 pages.
Diemoza et al., emozA method for high-energy, low-dose mammography using edge illumination x-ray phasecontrast imaging; published Nov. 28, 2016; 13 pages.
Schlenvoigt, A compact synchrotron radiation source driven by a laser-plasma wakefield accelerator; published on Dec. 9, 2007; 4 pages.
Kneip et al, Bright spatially coherent synchrotron X-rays from a table-top source; published on Oct. 24, 2010; 4 pages.
D. S. Coburn, Design, characterization and performance of a hard X-ray transmission microscope at the National Synchrotron Light Source II 18-ID beamline; publication date May 2019; 25 pages.
I A Vartanyants and a Singer, Coherence properties of hard x-ray synchrotron sources and x-ray free-electron lasers; publication date Mar. 31, 2010.
Graves et al, Compact x-ray source based on burst-mode inverse Compton scattering at 100 kHz; publication date Oct. 10, 2014; 25 pages.
Harbi et al., Design of a compact synchrotron for medical applications; published Apr. 2013; vol. 74, No. 4; 6 pages.
S. M. Hooker, Developments in laser-driven plasma accelerators; published in 2013, 11 pages.
Lima et al, Fast projection/backprojection and incremental methods applied to synchrotron light tomographic reconstruction; published in 2018; 9 pages.
Obara, Femtosecond time-resolved X-ray absorption spectroscopy of liquid using a hard X-ray free electron laser in a dual-beam dispersive detection method; published Jan. 13, 2014; 9 pages.
Ding, Femtosecond x-ray pulse temporal characterization in free-electron lasers using a transverse deflector, published Dec. 7, 2011; 6 pages.
Zehbe et al, Going beyond histology. Synchrotron micro-computed tomography as a methodology for biological tissue characterization: from tissue morphology to individual cells; published on Mar. 25, 2009; 11 pages.
Sprangle et al, High average current electron guns for high-power free electron lasers, published Feb. 14, 2011; 15 pages.
Marinelli et al, High-intensity double-pulse X-ray free-electron laser, published on Mar. 6, 2015; 6 pages.
Duan et al, High-Resolution Micro-CT for Morphologic and Quantitative Assessment of the Sinusoid in Human Cavernous Hemangioma of the Liver; published in Jan. 2013, vol. 8, Issue 1; 9 pages.
Makita et al, High-resolution single-shot spectral monitoring of hard x-ray free-electron laser radiation, published in Oct. 2015; 5 pages.
Computed Tomography; published Feb. 12, 2017; 12 pages.
Bartzsch et al, Influence of polarization and a source model for dose calculation in MRT; published in 2014; 17 pages.
Bennink et al, Influence of Thin Slice Reconstruction on CT Brain Perfusion Analysis; published on Sep. 11, 2015; 14 pages.
Qiongge Li et al., , Microbeam-Radiation-Therapy (MRT): Characterizing a Novel MRT Device Using High Resolution 3D Dosimetry; published in 2014; 86 pages.
Fischetti et at., Mini-beam collimator enables microcrystallography experiments on standard beamlines; published in 2009; 10 pages.
Eggl et al., Mono-Energy Coronary Angiography with a Compact Synchrotron Source; published in Feb. 9, 2017; 8 pages.
Bassey et al., Multiple energy synchrotron biomedical imaging system; published on Nov. 2, 2016; 20 pages.
Kozak et al., Optical gating and streaking of free electrons with sub-optical cycle precision; published on Jan. 25, 2017; 7 pages.
Lin et al., Optimization of image quality and acquisition time for lab-based X-ray microtomography using an iterative reconstruction algorithm; Mar. 8, 2018; 13 pages.
Properties of X-rays; PowerPoint presentation; 50 pages.
Wenz et al., Quantitative X-ray phase-contrast microtomography from a compact laser-driven betatron source; Jul. 20, 2015; 6 pages.
Andriyash et al., An ultracompact X-ray source based on a laser-plasma undulator; published on Aug. 22, 2014; 6 pages.
Altarelli et al., Structural biology at the European X-ray free-electron laser facility; 6 pages.
Grimm, Oliver, Synchrotron radiation for beam diagnostics: Numerical calculations of the single electron spectrum; Jun. 18, 2008; 33 pages.
Larrue et al., Synchrotron Radiation Micro-CT at the Micrometer Scale for the Analysis of the Three-Dimensional Morphology of Microcracks in Human Trabecular Bone; Jul. 2011, vol. 6, Issue 7; 12 pages.
Miao et al., Synchrotron Radiation X-Ray Phase-Contrast Tomography Visualizes Microvasculature Changes in Mice Brains after Ischemic Injury, vol. 2016; 9 pages.
Schneider et al., Synchrotron radiation: micrometer-sized x-ray beams as fine tools for macromolecular crystallography; Oct. 17, 2008; 5 pages.
Wiedemann, Helmut, Synchrotron Radiation; 142 pages.
Ice et al., The Race to X-ray Microbeam and Nanobeam Science; published on Dec. 2, 2011, vol. 334; 7 pages.
Yoon et al., Three-Dimensional Imaging of Hepatic Sinusoids in Mice Using Synchrotron Radiation Micro-Computed Tomography; Jul. 2013, vol. 8, Issue 7; 10 pages.
Haddad et al., Ultrahigh-Resolution X-ray Tomography; published on Oct. 13, 2015 vol. 266; 4 pages.
Carlton et al., Using Synchrotron Radiation Microtomography to Investigate Multi-scale Three-dimensional Microelectronic Packages; published on Apr. 13, 2016; 9 pages.
Li et al., Vestibular Organ and Cochlear Implantation—a Synchrotron and Micro-CT Study; Apr. 7, 2021; 12 pages.
Liu et al., Visualization and Pathological Characteristics of Hepatic Alveolar Echinococcosis with Synchrotronbased X-ray Phase Sensitive Micro-tomography; Nov. 29, 2016; 9 pages.
Vågberg, et al., X-ray phase-contrast tomography for high-spatial-resolutionze brafish muscle imaging; published on Nov. 13, 2015; 7 pages.
Eggl et al., X-ray phase-contrast tomography with a compact laser-driven synchrotron source, May 5, 2015, vol. 112, No. 18; 6 pages.

* cited by examiner

RADIOLOGIC BIOPSY SYSTEM AND METHOD

FIELD OF THE INVENTION

The invention generally relates to imaging systems and methods for radiologic imaging of biological specimens. More specifically, the invention relates to a system and method for cooperative imaging with conventional/standard computerized tomography (CT) and synchrotron radiation to rapidly localize and perform an image-based biopsy of tissue at a cellular or subcellular level.

BACKGROUND

In general, conventional, or medical CT scanners use a rotating X-ray tube and a row of detectors to measure X-ray attenuations by different tissues inside the body. CT is based on the fundamental principle that the density of the tissue passed by the X-ray beam can be measured from the calculation of the attenuation coefficient. Using this principle, CT allows the reconstruction of the density of the body, by 2-D sections perpendicular to the axis of the acquisition system.

The CT X-ray tube (typically with energy levels between 20 and 150 keV), emits N photons (monochromatic) per unit of time. The emitted X-rays form a beam which passes through the layer of biological material of thickness $\Delta x$. A detector placed at the exit of the sample, measures $N+\Delta N$ photons, $\Delta N$ smaller than 0. Attenuation values of the X-ray beam are recorded, and data used to build a 3-D representation of the scanned object/tissue. There are basically two processes of the absorption: the photoelectric effect and the Compton effect. This phenomenon is represented by a single coefficient. In the case of CT, the emitter of X-rays rotates around the patient and the detector, placed in diametrically opposite side, picks up the image of a body section (beam and detector move in synchrony). Unlike X-ray radiography, the detectors of the CT scanner do not produce an image. They measure the transmission of a thin beam (1-10 mm) of X-rays through a full scan of the body. The image of that section is taken from different angles, and this allows to retrieve the information on the depth (in the third dimension). The image of the section of the object irradiated by the X-ray is reconstructed from a large number of measurements of attenuation coefficient. It gathers all the data coming from the elementary volumes of material through the detectors. Using a computer and established algorithms, it presents the elementary surfaces of the reconstructed image from a projection of the data matrix reconstruction, the tone depending on the attenuation coefficients.

The multiple X-ray measurements taken from different angles are then processed on a computer system using reconstruction algorithms to produce tomographic (cross-sectional) images or virtual "slices." From the 2-D X-ray, a scan range is selected, and multiple tomographic slices are obtained.

During a traditional CT-guided biopsy, a so-called "scout view" is first generated which is essentially a general X-ray of the body, in order to identify a few key landmarks and roughly determine what level the area of concern is located and what area to scan. Then, a subsection (or scan range) is blocked off for slice acquisition.

Using conventional CT, a number of slices are obtained while the patient table is translated through the gantry. Each slice corresponds to a certain table position, and by extension, a certain position of the patient in the craniocaudal dimension. The ideal slice position is selected which displays the desired location to biopsy and the table is moved to that position. The remaining locations of the lesion can be determined from the image itself. A biopsy needle is then advanced, and the needle location is scanned incrementally to ensure correct trajectory within the plane of the initial slice. By virtue of that fact, however, the procedure remains invasive and still requires the use of a needle to ultimately obtain the tissue sample.

A CT machine for realizing noninvasive pathological diagnosis by using a synchrotron radiation light source has previously been proposed. However, there are limitations and obstacles heretofore inadequately addressed to make it practically useful. These obstacles can be divided into those resulting from inherent properties of the synchrotron light (also referred to as "synchrotron radiation") source and those related to the transition from fixable/inanimate specimens to living specimens. As to the former, the small cross-sectional size of the synchrotron light source renders it unsuitable for initial localization due to the large area that would need to be scanned and subsequent prohibitively long scan times. As to the latter, transition to living biological subjects present unique challenges, not the least of which is related to motion during scanning. Even the most minute of movements can interfere with obtaining the necessary data for cellular level resolution.

There are several challenges which have traditionally been associated with synchrotron radiation and limit its practicality and usefulness as a radiologic tool. To begin with, a synchrotron, which is a type of circular particle accelerator, is typically very large (some as large as a football field). Second is cost, with some synchrotrons costing up to $200 million just to build the actual device (not including housing, maintenance, etc.). Thus, there are only a few (less than 100) synchrotrons around the world. Synchrotron radiation is generated when relativistic charged particles (ex. electrons) are accelerated in a direction perpendicular to their velocity. This is accomplished through a series of magnets until they reach near the speed of light. These fast-moving electrons produce very bright light, called synchrotron light. The main properties of synchrotron light which set it apart from conventional ionizing radiation include high brilliance, high level of polarization, high collimation, low emittance, wide tunability, and pulsed light emission. This very intense light, predominantly in the X-ray region, is millions of times brighter than light produced from conventional sources and ten billion times brighter than the sun. Scientists can use this light to study minute matter such as atoms and molecules. Other practical differences between synchrotron light sources and conventional CT scanners are the following:

A. Synchrotron light can operate as a monochromatic beam (therefore eliminating beam hardening artifacts).

B. A synchrotron beam has a very small cross-section, with most synchrotrons generating a beam cross-section of only a few $mm^2$. There are exceptions, such as the Canadian Light Source synchrotron which can obtain a beam cross section up to ~130×9 $mm^2$ beam. However, there are only a few such facilities in the world capable of delivering similar larger sized beams. According to experts in the field, however, even this is not enough to scan, for instance, a chest of a swine unless it is a very small piglet. Certain techniques can be used to effectively enlarge the examined volume by translating a sample in the beam but then scan times become very long—sometime hours. At which point, its practicality on live specimens becomes a major concern, with issues such as motion artifact and the subsequent need for suppression measures such as respiratory-cardio gating.

C. An added critical difference from medical or conventional CT is that the sample must be rotated along its long axis. Consequently, it is very difficult to mount a sample on the CT stage—various contraptions must be devised to immobilize the sample (again, at this point, motion artifact becomes a major concern).

D. Synchrotron X-ray energy is limited to a range between approximately 100-140 keV. Comparatively, medical scanners can extend their range up to 250 keV.

Generally, synchrotron radiation excels in microscopy applications due to the small beam and very large photon flux density (ex. scanning a mice embryo, in which individual nuclei can be seen).

Therefore, there is opportunity and need for improvements in how to perform radiologic assisted biopsies including use of synchrotron radiation to provide a high-resolution image of potentially pathological specimens of living organisms, particularly suitable for detecting pathology in living humans.

SUMMARY OF THE INVENTION

The present invention couples conventional CT with synchrotron radiation as a substitute for needle based or invasive biopsy and is meant to generate a slice of similar scale as a histologic/pathologic slice. Once the desired location is determined by conventional CT scan, the patient or specimen is translated so that the lesion may be aligned with the synchrotron beam and permit scanning by synchrotron radiation. The patient is moved into position to permit synchrotron radiation to be applied to a very specific area, analogous to that which would be sampled in a needle biopsy. Synchrotron radiation allows for much thinner slice generation than conventional CT. The synchrotron beam would pass through that site and the "sample" is then obtained that will be of histologic (microscopic) slice thickness, i.e., a radiographic biopsy.

In a nonlimiting embodiment, the invention includes a method of performing a radiologic biopsy, including scanning a living human subject with a CT scanner to obtain CT scan images of the living human subject. Next is identifying in the CT scan images a localized area of potential pathology and identifying an X, Y and Z coordinates within the area of potential pathology. Contemporaneously with scanning the living human subject is scanning with a synchrotron radiation source the area of potential pathology at, or proximate to the X, Y and Z coordinates. Next is obtaining a dataset of sub-micron resolution image data from the scanning with the synchrotron radiation source. Another step is computer enabled resolving of the dataset to produce a radiographic image having cellular level resolution of at least a portion of the area of potential pathology.

The method of performing a radiologic biopsy may also include repositioning the living human subject before the step of scanning with the synchrotron radiation source to line up the X, Y and Z coordinates of the area of potential pathology with a beam of synchrotron radiation from the synchrotron radiation source.

The method of performing a radiologic biopsy may also include, during the step of scanning with the synchrotron radiation source, rotating the living human subject.

The method of performing a radiologic biopsy may also include, where the steps of scanning the living human subject with a CT scanner and scanning with the synchrotron radiation source are at least in part performed concurrently.

The method of performing a radiologic biopsy may also include where the radiographic image is of comparable quality to a histologic slice of at least a portion of the area of potential pathology.

The method of performing a radiologic biopsy may also include reviewing the radiographic image for evidence of pathology.

The method of performing a radiologic biopsy may also include tuning a synchrotron beam flux and energy from the synchrotron radiation source prior to the step of scanning with the synchrotron radiation source to ensure that the average energy is sufficient to penetrate through the living human subject but low enough to allow fast scans.

The method of performing a radiologic biopsy may also include where the CT scanner is a C-Arm CT scanner, and where the C-Arm CT scanner includes an unobstructed pathway for allowing a synchrotron radiation beam from the synchrotron radiation source to traverse the unobstructed pathway, where a direction of the synchrotron radiation beam and a direction of the scanning of the CT scanner are orthogonal to each other.

The method of performing a radiologic biopsy may also include where the steps of scanning the living human subject with a CT scanner and scanning with the synchrotron radiation source are at least in part performed concurrently while the synchrotron radiation traverses the unobstructed pathway.

The method of performing a radiologic biopsy may also include where the CT scanner is a horizontal CT scanner, where the horizontal CT scanner has an unobstructed pathway for allowing a synchrotron radiation beam from the synchrotron radiation source to traverse the unobstructed pathway.

The method of performing a radiologic biopsy may also include where the CT scanner is a horizontal CT scanner, where the living human subject is supported on a horizontal stage, where the horizontal stage is movable in an X, Y and Z direction, and where the horizontal stage is adapted to rotate in a rotisserie-type manner around an axis perpendicular to a plane of the horizontal CT scanner.

In a nonlimiting embodiment, a radiologic biopsy system of the invention includes a CT scanner adapted to scan a living human subject and provide CT scan images of the living human subject, where the CT scanner is adapted to provide an X, Y and Z coordinates of an area of potential pathology within the living human subject. The system also includes a synchrotron radiation source, where the synchrotron radiation source emits synchrotron radiation and is adapted to provide a synchrotron radiation scan of the potential pathology at, or proximate to the X, Y and Z coordinates. The synchrotron radiation can be emitted through a director, then through the living human subject, and then onto a receptor where the receptor collects data from the synchrotron radiation scan and communicates the data to a processing system adapted to process the data and provide a histologic slice of at least a portion of the area of potential pathology. The system also includes a stage adapted to hold the living human subject during both a CT scan and a synchrotron radiation scan.

The radiologic biopsy system may also include where the CT scanner is a C-Arm CT scanner, and where the C-Arm CT scanner includes an unobstructed pathway for allowing the synchrotron radiation from the synchrotron radiation source to traverse the unobstructed pathway to perform the synchrotron radiation scan of the living human subject.

The radiologic biopsy system may also include where the unobstructed pathway is an aperture in an arm of the C-Arm CT scanner.

The radiologic biopsy system may also include where the scan of the living human subject with a CT scanner and scan of the living human subject with the synchrotron radiation source are concurrently performable.

The radiologic biopsy system may also include where the CT scanner is a horizontal CT scanner, and where the horizontal CT scanner includes an unobstructed pathway for allowing the synchrotron radiation from the synchrotron radiation source to traverse the unobstructed pathway to perform the synchrotron radiation scan of the living human subject.

The radiologic biopsy system may also include where the CT scanner is a horizontal CT scanner, where the stage is horizontal and movable in an X, Y and Z direction, and where the stage is adapted to rotate in a rotisserie-type manner around an axis perpendicular to a plane of the horizontal CT scanner.

The radiologic biopsy system may also include where a direction of the synchrotron radiation and a direction of the scanning of the CT scanner are orthogonal.

The radiologic biopsy system may also include where the director includes one or more of a series of reflectors, refractors, slits, collimators and radiation shutters capable of directing and altering characteristics of the synchrotron radiation.

The radiologic biopsy system may also include where the director comprises fiberoptics adapted to transmit the synchrotron radiation, and where the synchrotron radiation source is remotely located to the CT scanner.

In another nonlimiting embodiment of the invention, a radiologic biopsy system includes a CT scanner adapted to scan a living human subject and provide CT scanned images of the living human subject, where the CT scanner is adapted to provide an X, Y and Z coordinates of an area of potential pathology within the living human subject. The system also includes a synchrotron radiation emitter, where the synchrotron radiation emitter emits synchrotron radiation and is adapted to provide a synchrotron radiation scan of the potential pathology at, or proximate to the X, Y and Z coordinates, where the synchrotron radiation is emittable through a director, then through the living human subject, and then onto a receptor where the receptor collects data from the synchrotron radiation scan and communicates the data to a processing system adapted to process the data and provide an image of histologic slice quality of at least a portion of the area of potential pathology.

These, as well as other components, steps, features, objectives, benefits, and advantages, will now become clear from a review of the following detailed description of illustrative embodiments, the accompanying drawings, and the claims.

BRIEF DESCRIPTION OF THE DRAWINGS

Advantages of the invention will be readily appreciated as the same becomes better understood by reference to the following detailed description when considered in connection with the accompanying drawings, wherein.

Figure 1:
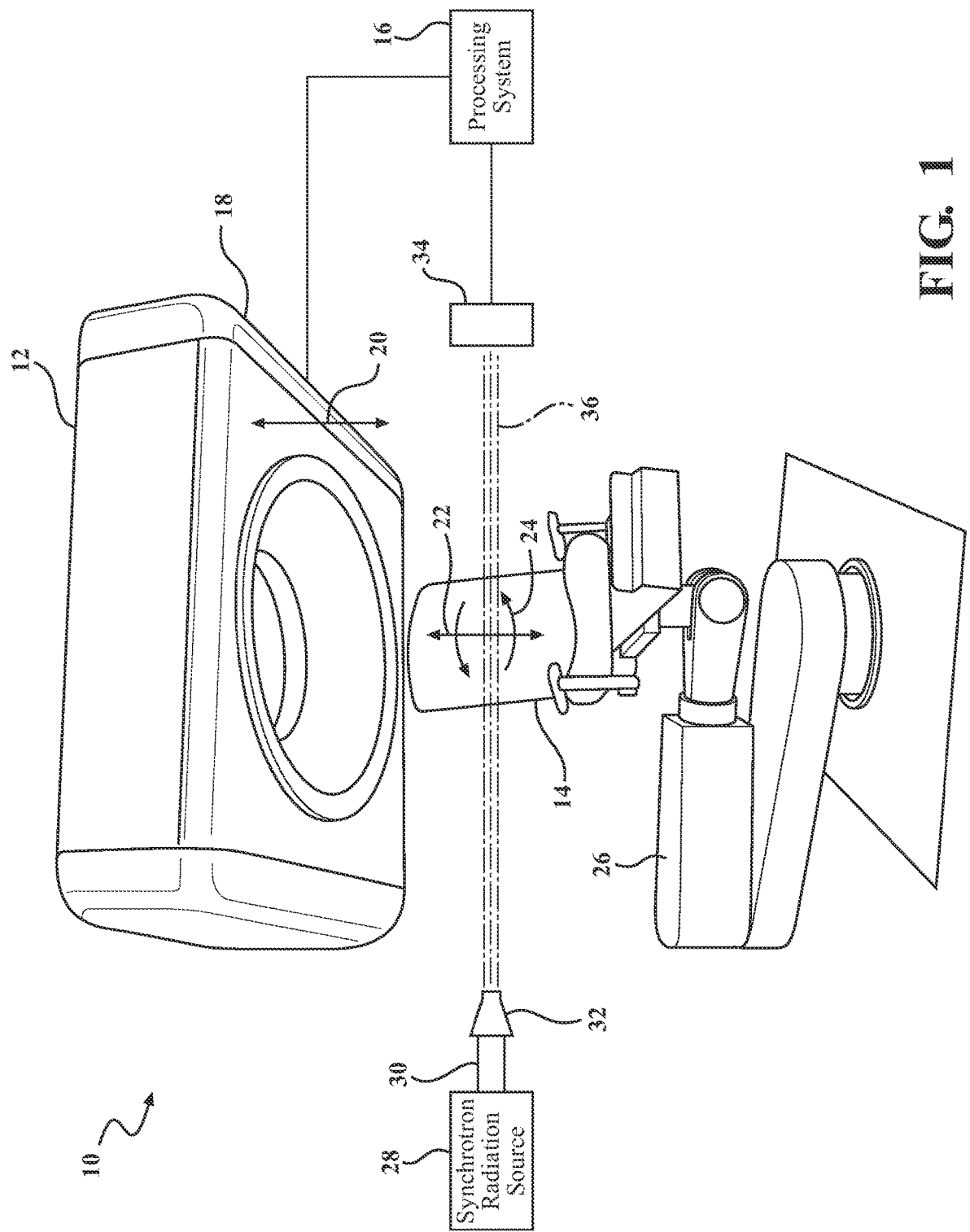
FIG. 1 is a schematic-type perspective view of a first embodiment of a CT and synchrotron radiation cooperative scanning system of the invention with a vertical CT scanner.

For the purposes of promoting an understanding of the principles of the embodiments, reference will now be made to the embodiments illustrated in the drawings and specific language will be used to describe the same. It will nevertheless be understood that no limitation of the scope of the embodiments is thereby intended. Any alterations and further modifications in the described embodiments, and any further applications of the principles of the embodiments as described herein are contemplated as would normally occur to one skilled in the art to which the embodiment relates.

DETAILED DESCRIPTION OF THE DRAWINGS

The present invention is a CT guided and synchrotron radiation performed radiographic biopsy system and method. The invention has several similarities to a CT-guided biopsy. As mentioned previously, during CT-guided biopsy, a needle is used to obtain a sample. However, in contradistinction, the proposed invention substitutes a needle with a synchrotron radiation-based image to ultimately obtain a "sample." The present invention combines a standard diagnostic CT to locate the area of concern (ex. a lesion) and then subsequently apply synchrotron radiation to produce an image equivalent to a specimen that would be examined on a slide. The combined system of conventional CT and synchrotron radiation can be used to produce a histologic/pathologic slice thickness of any area of the human body (ex. the otic capsule of the inner ear, nephrons which are functional units of the kidney, etc). It is believed that there is wide beneficial application of the invention. However, it seems that the described system and methods for performing a radiologic biopsy have a particular utility in sampling potentially cancerous lesions.

Important benefits of the invention include greater patient comfort, elimination of risks associated with needle biopsy such as infection or nerve damage, and reduced time to complete the procedure thus leading to quicker diagnoses.

The system and method include combining standard diagnostic CT type radiation with synchrotron radiation to obtain histologic/pathologic slice thickness samples of subject's body. This certainly has a myriad of applications, but one of the primary applications is with regards to obtaining pathology samples, as in the case of image guided biopsies. The patient would undergo a standard preliminary CT scan to determine where the lesion is. Once determined, they would be moved to the appropriate position. Then the synchrotron beam can be used to pass through that site and the "sample" could then be obtained that would be of histologic slice thickness.

Next, described is a general setup of the combined standard CT/synchrotron CT method and apparatus. There are multiple methods that can be used to combine a synchrotron radiation source and standard/medical CT scanner into a single apparatus. The primary utilities in combining the two in the manner described below is speed of localization, quality of image rivaling histologic studies, and less burden on the patient. For most of the described embodiments it is assumed that synchrotron beamlines are in a fixed position relative to the standard CT machine.

Option 1: Perform both the CT scan and synchrotron scan with a subject in a vertically held position. In this embodiment, the subject and sample must be rotated along its long axis (such as on a rotisserie). Thus, a platform capable of rotating 360 degrees is used. As a consequence of this rotation, it is easier to accomplish if the patient is standing or sitting.

In this scenario, the patient is placed in a vertically oriented CT scanner, with the synchrotron beam at an orthogonal angle relative to the standard CT beam.

The patient will stand on a platform capable of moving vertically, as well as in the Z direction. Additionally, the platform can rotate 360 degrees. The CT scanner itself can be a dedicated vertical CT, a vertically movable CT, or a C-Arm CT. The patient is advanced through the scanner vertically (as in a regular CT), in order to obtain the X-Y (i.e., transverse and craniocaudal dimensions respectively) coordinates of a particular area of interest.

Once the patient is in the desired X-Y plane, the Z-coordinate (i.e., depth or anteroposterior dimension) must be determined. There is more than one way to calculate the Z-coordinate/depth known to those skilled in the art. One is manually (which is already done in CT-guided biopsies). A second method would be to rely on parallax shift. In this method, the C-Arm X-ray tube is used to generate a pair of images +15° and −15° relative to the 0° position. A third method is to use an automated software to determine the depth and its reference to the synchrotron beam. In this latter scenario, the region of interest could be selected, and the depth automatically calculated, and patient translated in the Z dimension to be in line with the synchrotron beam.

Once the X, Y, and Z coordinates are determined, the patient is moved to the appropriate Z-plane which will be in the path of the synchrotron beam. Once directly in the path of the synchrotron beam, the patient is rotated 180-360 degrees and a synchrotron-based image of the lesion in question is obtained (for example, on the microscopic or submicroscopic scale).

Option 2: Use a horizontally oriented standard CT scanner followed by a synchrotron scan. This method is likely possible but much more cumbersome because the patient must be rotated along their long axis, which requires support to keep the patient from falling off the bed. The platform (or gantry) can move forwards and backwards, and adjust height/depth, as well as rotate along its long axis. Consideration is needed so that supports do not obstruct the synchrotron beam. The remainder of the steps are essentially the same as in the first option.

Certain measures can be put in place to reduce motion artifact during scanning. These may include respiratory-cardio gating or physical stabilizers such as straps or padding. In certain instances (such as scanning in the lung), active breath control can also be used.

Synchrotron beam flux and energy are tuned depending on the beam width, prior to synchrotron scanning, to ensure that the average energy is sufficient to penetrate through the sample but low enough to allow fast scans. Energy tuning can be performed using various filters, such as molybdenum and copper. Materials such as fused silica bar attenuators allow for adjusting the beam flux and profile. To preserve beam coherence prior to scanning, filters and optics are made of high-quality mirror polished materials (ex. Pf6/IF1 beryllium) to ensure material homogeneity (flux and beam profile tuning). Scintillators must be as dense as possible while not degrading the resolution. Briefly, a scintillator is a material that converts a radial ray such as an X-ray into visible light. Thickness of the scintillators are optimized to provide a compromise between light output and maximum optical resolution for each X-ray optic. The thickness of the scintillator results in a trade-off between absorption and spatial resolution. Thicker scintillators absorb a larger proportion of X-rays but allow for greater scatter and therefore poorer spatial resolution. The reason thicker scintillators are preferred in synchrotron radiation is to optimize signal (while obviously keeping spatial resolution at an acceptable range). Various optics can be selected depending on the beam width (ex. 25-6 µm/voxel). Photodarkening refers to an optical effect in the interaction of laser radiation with amorphous media (ex. Glass) in optical fibers. It limits the density of excitations in fiber lasers and amplifiers. In order to prevent optics darkening prior to scanning, particularly at smaller beam widths, optics can be intrinsically hardened with X-rays, or are protected from darkening using a thin glassy carbon mirror to reduce internal scattering and lead glass in the front of an optic to stop as much scattering as possible. A beam stop can be used to prevent beam back scatter during scanning. More specifically, it is meant to block the X-ray beam directly transmitted by the sample to protect the detector, as well as oversaturation of the detector. In the case of a synchrotron, it can be made of a hollow tungsten cylinder. It is typically placed inside the flight tube just before the big Kapton window (Kapton is a polymer commonly used as a material for windows used with all kinds of X-ray sources. Its high mechanical and thermal stability as well as high transmittance of X-rays make it the preferred material. It is also relatively insensitive to radiation damage). Curing can be performed after scanning in order to ensure optics recovery, in the event of optics darkening. Curing refers to a photochemical process in which high-intensity ultraviolet light or LED light is used to instantly cure or "dry" inks, coatings or adhesives. It is used to initiate a photochemical reaction that generates a cross-linked network of polymers.

Synchrotron scanning can be made to work similarly to conventional CT scanning in terms of how projections are reconstructed to create a virtual slice. Multiple projections are obtained while the specimen is rotated 180-360 degrees. To translate the data into a 2-D image, tomographic reconstruction is performed using algorithms already in use with conventional CT. All reconstruction algorithms rely on a Radon transformation, which is represented by the function $f(x, y)$ and can be defined as a series of line integrals through $f(x, y)$ at different offsets from the origin. This is defined mathematically as: whose value at a particular line is equal to the line integral of the function over that line: $R(r,\theta) = \int_{-\infty}^{\infty} \int_{-\infty}^{\infty} f(x,y) \delta(x \cos\theta + y \sin\theta - r) dx\, dy$.

There are several reconstruction algorithms that can be used. However, the most common include Fourier-Domain reconstruction, back/filter-back projection and iterative reconstruction. These methods are known to those skilled in the art as being used in synchrotron CT scanning, including microscopic applications. Artisans and their articles discussing reconstruction algorithms and related issues include: Pacureanu, Imaging The Bone Cell Network With Nanoscale Synchrotron Computed Tomography, 2013, page 173; Schleede, Simone, X-ray Phase-Contrast Tomosynthesis For Improved Breast Tissue, European Journal of Radiology, 2013, pages 531-536; Zhao, Yuqing, An Iterative Image Reconstruction Algorithm combined with forward and backward diffusion filtering for in-line x-ray phase contrast Computed Tomography, Journal of Synchrotron Radiation, 2018, pages 1450-1459; Duan, Jinghao, High-Resolution Micro-CT for Morphologic and Quantitative Assessment of the Sinusoid in Human Cavernous Hemangioma of the Liver, PLOS, 2013; Vagberg, William, X-ray Phase-Contrast Tomography for High-Spatial-Resolution Zebrafish Muscle Imaging, Scientific Reports; Bennink, Edwin, Influence of Thin Slice Reconstruction on CT Brain Perfusion Analysis, PLoS ONE; and Sprawls, Perry Physical Principles of Medical Imaging. 2nd ed, Aspen Publishers, 1985. The above referenced resources are included here as illustrative of how and why the reconstruction algorithms are known to those skilled in the art.

For example, in filtered-back projection, the original image is $\mu(x, y)$ and the back-projection image is: $f_{fbp}(x, y) = \int q_0(x \cos\theta + y \sin\theta) d\theta$ with $q_\theta(t) \int p_\theta(\omega) |\omega| e^{j2\pi\omega t} d\omega$. It has also been demonstrated and known, that using a filter back projection algorithm can eliminate artifacts such as blurring. It has also been shown that for the high-resolution imaging, the source-object-distance and the object-detector-distance can be optimized to obtain the desired magnification onto the detector. The number of projections, step angle and exposure time per projection and a voxel size can be adjusted.

When a synchrotron beam passes through the specimen (for example a live patient), it inevitably traverses the entire width of the patient at that level. This means that when the synchrotron image is generated, it includes not just the lesion in question, but also tissue along the entire trajectory of the synchrotron beam (i.e., tissue that is outside the area of interest). The issue then becomes determining what area along the length of the synchrotron image corresponds to the lesion seen on the conventional CT image. There are a few ways to resolve this issue. In conventional CT, it is already known to those skilled in the art that thicker slices can be reconstructed from thinner slices (not vice versa however). Thus, one method is to reconstruct the synchrotron image according to the same thickness as the conventional image and then direct correlation to the conventional image can be made. A second method known to those skilled in the art relies on the fact that the initial conventional CT image is displayed as a grid of pixels, with each pixel assigned certain X and Y coordinates. Additionally, a pixel has a determined height and width (pixel size can be calculated by dividing the field of view by the matrix size). The area or lesion in question will correspond to a certain set of pixels (i.e., specific area on the pixel grid). The synchrotron beam will already be localized to approximately the Y dimension. The synchrotron pixel dimensions are also known and therefore the absolute distance, or X dimension, can be determined from a common reference point. One can then calculate/convert the synchrotron pixel distance that would correspond to that on the conventional CT image. A third method involves calibrating the overlapping scan regions with gradual transition and normalization of the gray levels in the area common to the two scans.

The result is an image (or set of images) of comparable resolution and scale to substitute for a cellular or subcellular sample examined under a microscope. For example, if a patient was found to have an incidentally discovered pulmonary nodule on a conventional screening CT of the chest. The patient would then undergo radiologic biopsy, with localization and subsequent synchrotron scanning to obtain a histologic level slice thickness and scale to determine if malignant cells are in fact present or not. An additional example would be in a patient with known cirrhosis with an indeterminate liver lesion, questionable for hepatocellular carcinoma. Using the same process, it could be determined if HCC is present or not. Radiologic biopsy could also be used in non-malignancy type cases. For example, in determining if there is ongoing rejection versus some other process in renal transplant patients or examining the inner ear (ex. cochlea) in patients with idiopathic hearing loss.

Additional nonlimiting embodiments of the invention can use other sources of synchrotron radiation, such as a free electron laser (FEL), or alternatively, a more compact version of a synchrotron. In the case of a FEL, it uses the same principal as a standard circular synchrotron. In that, synchrotron radiation is generated when a relativistic particle is accelerated in a direction perpendicular to their velocity. Where a FEL differs from a typical circular accelerator is that an electron beam traversing an undulator interacts with a co-propagating photon beam of the correct wavelength which induces bunching of the electron beam, giving rise to coherent emission. In any of the above cases, whether conventional circular accelerator, compact circular accelerator, or a FEL, the principal is the same, in that the synchrotron radiation source is used in cooperation with conventional CT.

As mentioned in a previous section, synchrotrons are large and few in number, therefore limiting their availability. And as can be inferred from the previously proposed constructs, conventional CT seems to be necessarily "tethered" to the synchrotron. Consideration can therefore be given to synchrotron radiation that is distant from its parent source, i.e., untethering the synchrotron source in order to increase availability/access. One such proposed method involves the use of fiberoptics which could theoretically transmit synchrotron radiation over long distances and thereby remove the need to be directly tethered to a particle accelerator (i.e., siphoning synchrotron radiation). The main challenges in transmitting synchrotron light over optical fibers relate to what are called "coupling efficiency" and "dispersion" which are introduced during propagation along the fiber. These two factors are strictly correlated when one is trying to design such a system: since there are minimum requirements on the signal-to-noise ratio, if the coupling efficiency is too low, one is forced to couple light on a larger bandwidth, which in turn makes the dispersion worse, for example. The basic components of a generic fiberoptics-based system include the synchrotron light source, a couple/collimator, with or without a light sampling component at the beginning of the fiber, and the sample at some predetermined distance from the original source and at the end of the fiber propagation.

Now with reference to FIG. 1, in a nonlimiting embodiment, a first radiologic biopsy system 10 of the invention includes a vertical CT scanning system 12 and a vertical presenting stage/platform 14 for supporting a patient (not shown) to be scanned. The CT scanning system 12 is of the type well known to those of skill in the state of the art and is capable of providing slices of adequate resolution and to identify an X, Y and Z coordinates of an area of a mass/lesion or other potential pathology warranting further investigation through biopsy. The CT scanning system 12 is connected to, or otherwise in communication with a processing system 16 for receiving radiologic imaging data and processing it to produce radiographic slices of the subject of interest. The processing system 16 includes a computer system and software of the type well known to those of skill in the art. The processing system 16 is capable of taking data, including a dataset resulting from a CT scan, and process it into radiographic images reviewable by a radiologist and others. The CT scanning system 12 includes a CT scanner 18 that may be capable of moving in a vertical direction 20, with the patient seated or standing on the stage/platform 14. The platform 14 may also be capable of moving in a vertical direction 22, as well as in the X and Z-plane directions, in addition to moving rotationally 24. In an embodiment, only the stage/platform 14 will move and the CT scanner 18 will remain stationary. The movement of the stage/platform 14 is directed by an articulating apparatus 26 capable of moving the stage/platform 14 at least in a vertical direction, in the Z-plane, and rotationally. The stage/platform 14 is depicted as one allowing for the subject to be seated in during the procedure. It is also possible for the stage/platform 14 to allow the subject to stand upright.

The radiologic biopsy system 10 further includes a synchrotron radiation source 28. The synchrotron radiation source 28 includes at least a synchrotron such as the Canadian Light Source synchrotron located in Saskatoon in the Province of Saskatchewan, Canada or the National Synchrotron Light Source II (NSLS-II) at Brookhaven National Laboratory (BNL) in Upton, N.Y. Any other similarly equipped synchrotrons are suitable. It is also anticipated that the synchrotron radiation source 28 is an alternatively derived source for synchrotron radiation that meets the requirements for providing beamwidth and other characteristics suitable for the intended purpose. Alternative synchrotron radiation sources are described above.

The synchrotron radiation source 28 generates synchrotron radiation to a director 30 and then to an emitter 32. The director 30 and emitter 32 are at least an aperture from the synchrotron or may be series of reflectors, refractors, slits, collimators and radiation shutters capable of directing and altering characteristics of the synchrotron radiation. As described above, in an alternative embodiment the director 30 may also include fiberoptics suitable for directing the synchrotron radiation at a distance from the synchrotron radiation source 28.

Opposite of the emitter 32 is a receptor 34 for receiving the radiation after passing through the subject. The receptor 34 is in communication with the processing system 16 for processing the data resulting from the synchrotron radiation scan. The processing system 16 is illustrated as the same for both the CT scanning system 12 and the synchrotron radiation source 28 but it should be understood that the systems could be separate. The processing system 16 includes computer hardware and software known to those of skill in the art and is capable of taking data including a dataset resulting from a synchrotron scan and process it into radiographic images reviewable by a radiologist and others.

In operation of the radiologic biopsy system 10, the subject, such as a patient with potential pathology warranting a biopsy study is positioned on the stage/platform 14 in a seated or standing position. The CT scanning system 12 is then activated to provide slices of the patient around the area of interest. A review of the slices enables determining a more precise location requiring further study. This may be done by a radiologist. Next, an X, Y and Z coordinates of the area requiring further study are determined from the table position and the provided CT slices. The patient is then optimally positioned via the stage/platform 14 to allow a synchrotron radiation 36 from the synchrotron radiation source 28 to be radiated directly at the X, Y and Z coordinates of the area requiring a biopsy. The data received from the receptor 34 is then processed by the processing system 16. The radiologic biopsy system 10 thereby provides a high-resolution scan of a very specific area of the subject thus allows for looking at the tissue such as cells and determining if pathology is present. In this respect, the system allows for performing an important medical procedure without the invasiveness and risk associated with a needle biopsy.

Figure 2:
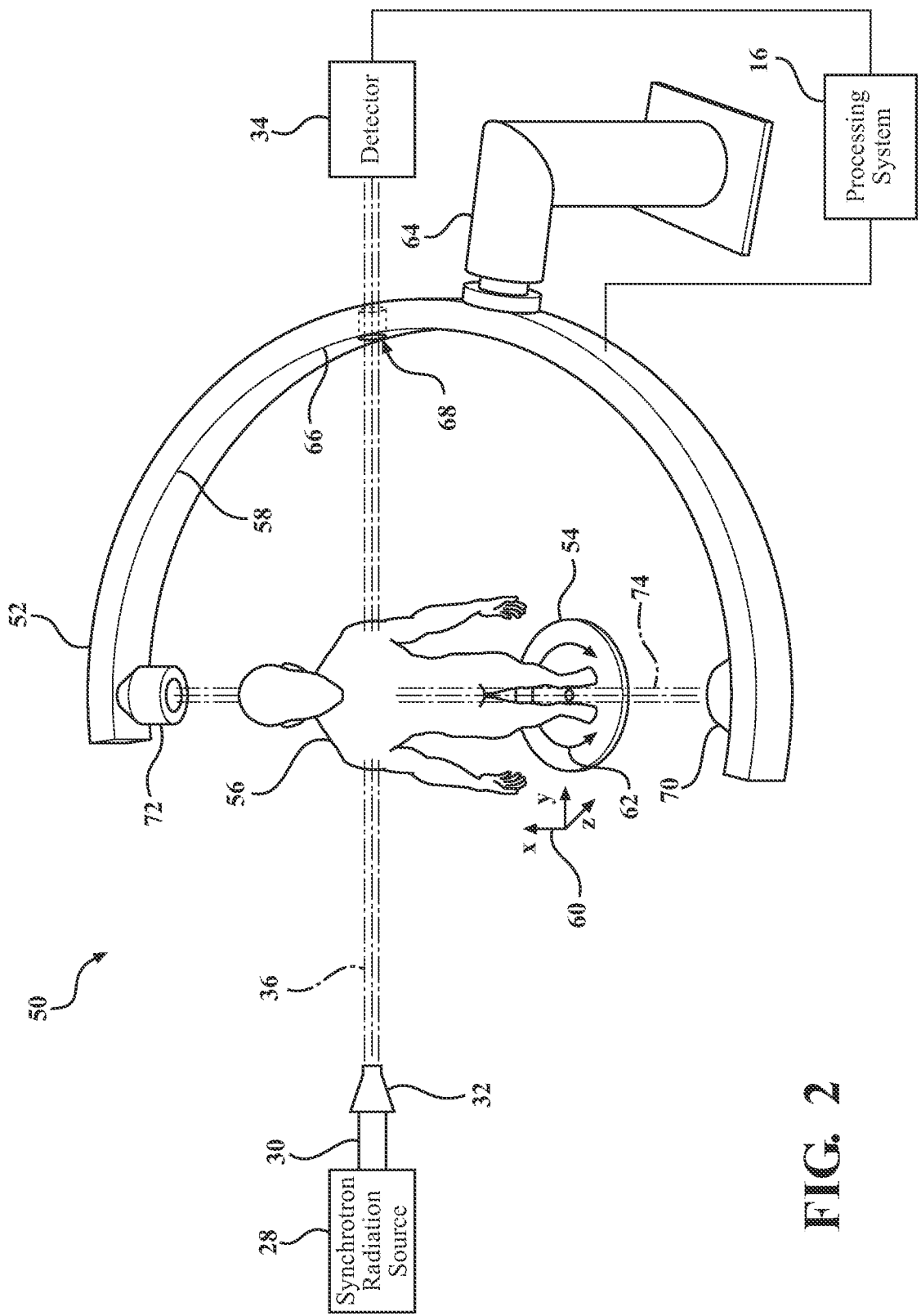
FIG. 2 is a schematic-type perspective view of a second embodiment of a CT and synchrotron radiation cooperative scanning system of the invention with a C-Arm CT scanner.

Referring to FIG. 2, in a nonlimiting embodiment, a second radiologic biopsy system 50 of the invention includes a C-Arm CT scanning system 52 and a vertical presenting stage/platform 54 for supporting a patient 56 to be scanned. The C-Arm CT scanning system 52 is of the type well known to those of skill in the state of the art and can provide slices of adequate resolution and to identify an X, Y and Z coordinates of an area of a mass or other potential pathology warranting further investigation through biopsy. The C-Arm CT scanning system 52 offers the advantage of not including a fully circular apparatus around the patent thus providing easier access for integrating with a synchrotron radiation source. The C-Arm CT scanning system 52 is connected to, or otherwise in communication with a processing system 16 for receiving radiologic imaging data and processing it to produce radiologic slices of the subject of interest. The C-Arm CT scanning system 52 includes a CT scanner 58 which has a connecting element capable of moving horizontally, vertically and around the swivel axes, so that X-ray images of the patient can be produced from almost any angle. The stage/platform 54 can move in a X, Y and Z direction 60, in addition to moving rotationally 62. The movement of the CT scanner 58 is directed by an articulating apparatus 64 capable of moving the CT scanner at least in a vertical direction. The stage/platform 54 is depicted with the patient 56 standing on the stage/platform but could also include a vertically oriented stage/platform for holding the patient in place with the patent's back to the stage/platform 54. The stage/platform 54 includes technology known to those skilled in the art and is capable of precise and steady movements to help reduce motion artifact.

The radiologic biopsy system 50 further includes a synchrotron radiation source 28. The synchrotron radiation source 28 includes any of the sources as previously described. The synchrotron radiation source 28 generates synchrotron radiation to the director 30 and then to the emitter 32. The director 30 and emitter 32 are at least an aperture from the synchrotron or may be series of reflectors, refractors, slits, collimators and radiation shutters capable of directing and altering characteristics of the synchrotron radiation. As described above, in an alternative embodiment the director 30 may also include fiberoptics suitable for directing the synchrotron radiation at a distance from the synchrotron radiation source 28.

Opposite of the emitter 32 is a receptor 34 for receiving the radiation after passing through the patient 56. The receptor 34 is in communication with the processing system 16 for processing the data resulting from the synchrotron radiation scan. The arm 66 of the CT scanner 58 includes an aperture 68 of suitable size to allow the synchrotron radiation 36 to pass through the arm 66 and reach the receptor 34. The aperture 68 could be an actual opening or an unobstructed pathway including where a material is used that will not significantly interfere with the synchrotron radiation. The CT scanner 58 includes an X-ray emitter 70 and an X-ray receptor 72 opposite the X-ray emitter 70. The X-ray emitter 70 emits X-rays 74 in a direction through the patient 56 to identify the area of interest.

In operation of this nonlimiting embodiment of the radiologic biopsy system 50, the patient 56 requiring a biopsy is positioned on the stage/platform 54 in a seated or standing position. The C-Arm CT scanning system 52 is then activated to provide radiographic slices of the patient around the area of interest. A review of the slices enables determining a more precise location in the patient requiring further study. This may be done by a radiologist. The C-Arm CT scanning system 52 determines an X, Y, and Z coordinates of the area requiring further study. The patient is then moved via the stage/platform 54 so that the synchrotron radiation 36 from the synchrotron radiation source 28 is radiated directly at or near the X, Y and Z coordinates of the area requiring a biopsy. The CT scanner 58 is positioned to allow the synchrotron radiation 36 to be orthogonal to the CT scanner radiation 74 so that synchrotron radiation passes through the aperture 68. The data received from the receptor 34 is then processed by the processing system 16. The radiologic biopsy system 50 thereby provides a high-resolution scan of a very specific area of the patient thus allows for looking at the tissue such as cells and determining if pathology is present.

Importantly, in this embodiment, movement of the CT scanner 58 in cooperation with movement of the stage/gantry 54 allows for positioning the patient 56 precisely such that both the CT scan and synchrotron radiation scan can be performed simultaneously in the area to be biopsied. After the patient 56 is in the appropriate position to perform the synchrotron radiation scan both the CT scan and synchrotron radiation scan can take place concurrently or in phases to identify and focus in on the area requiring biopsy. Further, during both the CT scan and synchrotron radiation scan the patient can be rotated on stage/platform 54 to allow for correlating the image and providing at least a 2-D image where the synchrotron radiation scan provides a histologic (microscopic) slice thickness of the area of interest resulting in a radiographic biopsy.

Figure 3:
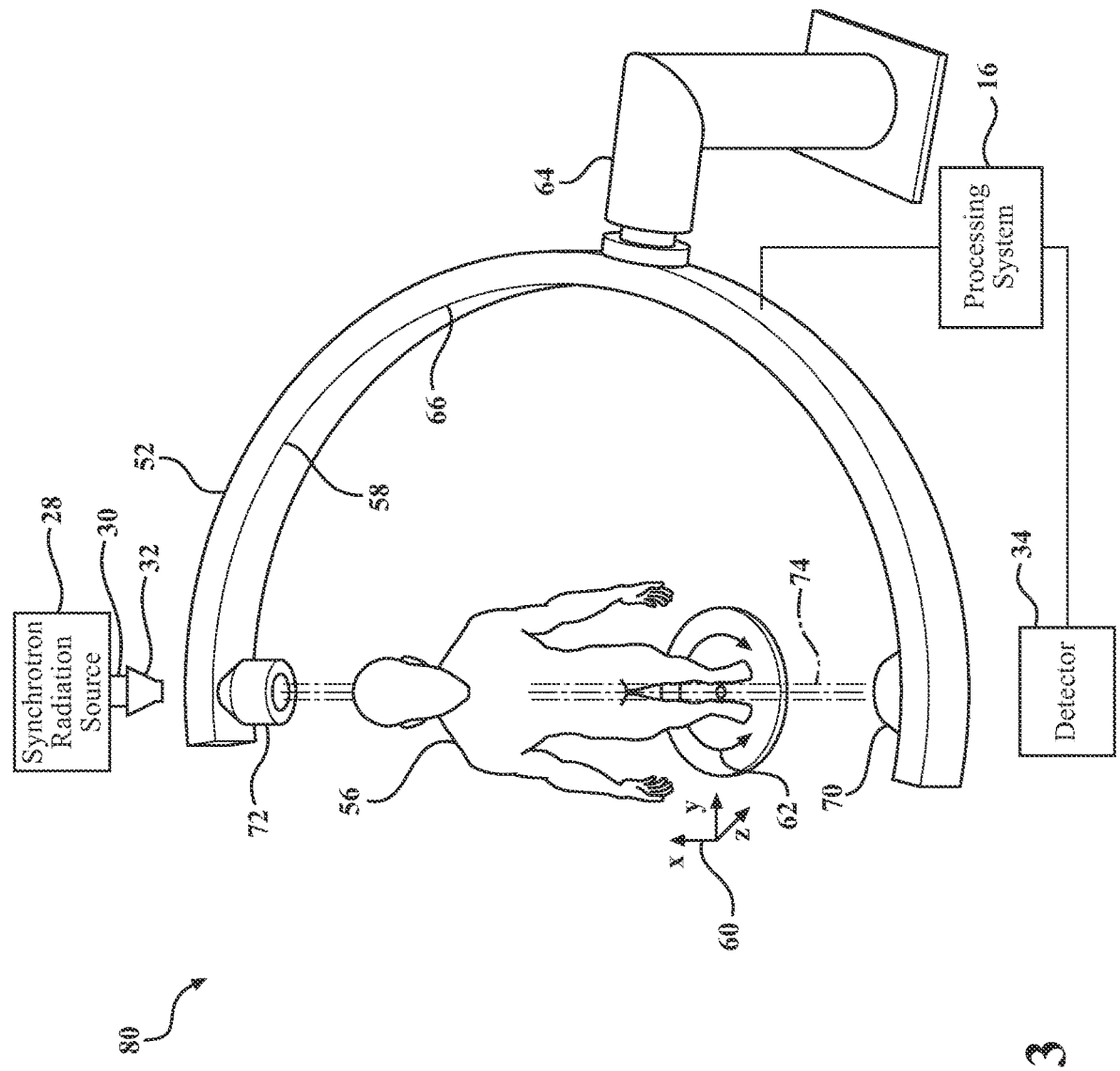
FIG. 3 is a schematic-type perspective view of a third embodiment of a CT and synchrotron radiation cooperative scanning system of the invention with a C-Arm CT scanner.

Now with reference to FIG. 3, in another nonlimiting embodiment, a third radiologic biopsy system 80 of the invention is similar to what is described in relation to FIG. 2, but with the synchrotron radiation source 28 and receptor 34 being aligned relative to the X-ray emitter 70 and an X-ray receptor 72 so that the synchrotron radiation 36 will be parallel to the CT scanner radiation 74. In this embodiment, no modification to the C-Arm CT scanning system 52 is needed to allow the synchrotron radiation to traverse the patient 56.

In operation of the radiologic biopsy system 80, the patient 56 requiring a biopsy is positioned on the stage/platform 54 in a seated or standing position. As described in relation to FIG. 2, the C-Arm CT scanning system 52 is then activated to provide slices of the patient around the area of interest and review of the slices enables determining a more precise location in the patient requiring further study. In this embodiment, the patient 56 is then moved via the stage/platform 54 up or down so that the synchrotron radiation 36 from the synchrotron radiation source 28 is radiated directly at or proximate the X, Y and Z coordinates of the area requiring a biopsy. In this embodiment, movement of the CT scanner 58 in cooperation with movement of the stage/platform 54 allows for positioning the patient 56 precisely such that the CT scan and synchrotron radiation scan can be performed in close sequence, first by CT scan to isolate the area of interest and then moving the patient at least linearly up or down to accommodate the distance between the CT scan beam and the synchrotron scan beam to perform the synchrotron radiation scan on the area requiring biopsy. Once in position, during synchrotron radiation scan the patient can be rotated on the stage/platform 54 to allow for correlating the image and providing at least a 2-D image where the synchrotron radiation scan provides a histologic (microscopic or submicroscopic) slice thickness of the area of interest resulting in a radiographic biopsy.

Figure 4A:
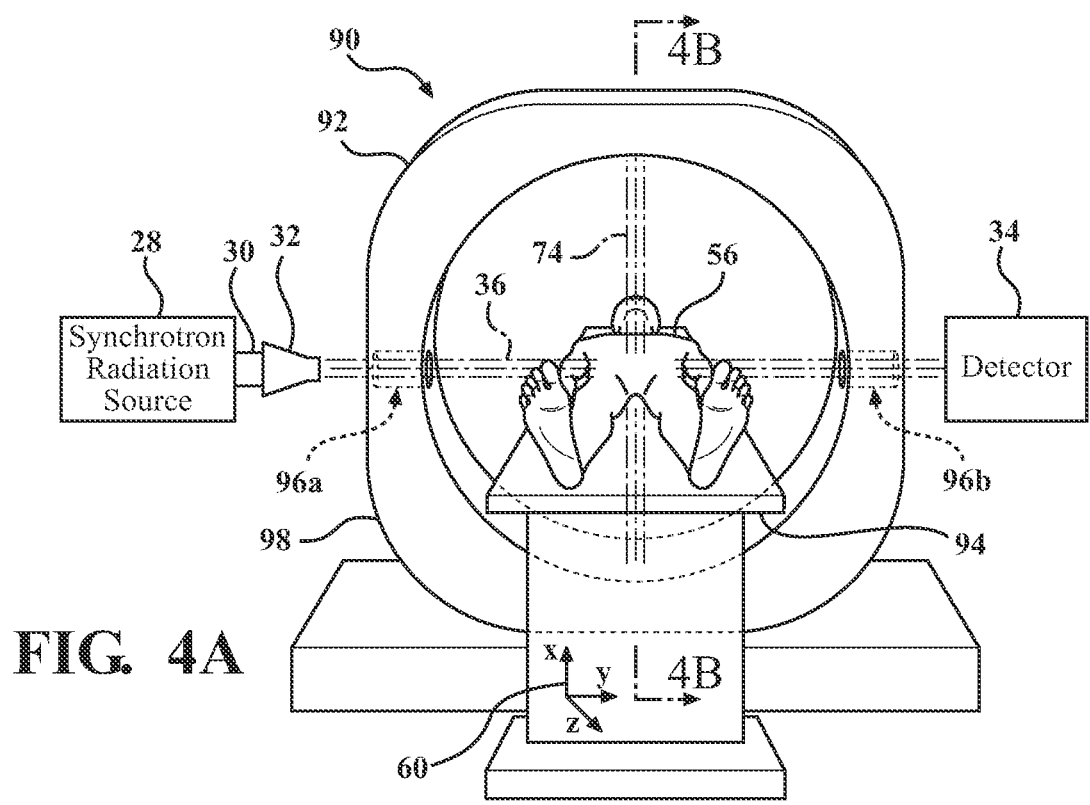
FIG. 4A is a schematic-type perspective view of a fourth embodiment of a CT and synchrotron radiation cooperative scanning system of the invention with a horizontal CT scanner.
Figure 4B:
FIG. 4B is cutaway of the fourth embodiment of FIG. 4A along the lines 4B-4B.

With reference to FIGS. 4A and 4B, in yet another nonlimiting embodiment, a fourth radiologic biopsy system 90 of the invention includes a horizontal CT scanning system 92 and a horizontal bed 94 for supporting the patient 56 to be scanned. The horizontal bed 94 can move in at least an X, Y and Z direction. The bed 94 may also be able to rotate in a rotisserie-type manner around an axis perpendicular to a plane CT scanning system 92.

The horizontal CT scanning system 90 is of the type well known to those of skill in the art and is capable of providing slices of adequate resolution and to identify an X, Y and Z coordinates of an area of a mass or other potential pathology warranting further investigation through biopsy. Similar to the C-Arm CT scanning system described in reference to FIG. 2, the system is connected to or otherwise in communication with a processing system (not shown) for receiving radiologic imaging data and processing it to produce radiologic slices of the patient.

The horizontal CT scanning system 90 includes a first and second aperture 96a, 96b for allowing synchrotron radiation 36 to pass through part of a housing 98 of the horizontal CT scanning system 90. Advantageously, the first and second aperture 96a, 96b may be a true aperture or a portion of the housing 98 with no obstacles or other X-ray interfering properties. In this embodiment, CT scan X-rays 74 are orthogonal to the synchrotron radiation 36.

In operation of this nonlimiting embodiment of the radiologic biopsy system 90, the patient 56 requiring a biopsy is positioned on the bed 94 in either a prone or supine position. The horizontal CT scanning system 92 is then activated to provide slices of the patient around the area of interest. A review of the slices enables determining a more precise location in the patient requiring further study. The system 90 determines an X, Y, and Z coordinates of the area requiring further study. The patient is then moved via the bed 94 so that the synchrotron radiation 36 from the synchrotron radiation source 28 is radiated directly at the X, Y and Z coordinates of the area requiring a biopsy. Due to the configuration of the system 90 the horizontal CT scanner 92 is positioned to allow the synchrotron radiation 36 to be orthogonal to the CT scanner radiation 74 as the synchrotron radiation passes through the apertures 96a, 96b. The data received from the receptor 34 is then processed by the processing system. The radiologic biopsy system 90 thereby provides a high-resolution scan of a very specific area of the patient thus allows for looking at the tissue such as cells and determining if pathology is present.

In this embodiment, movement of the bed 94 allows for positioning the patient 56 precisely such that both the CT scan and synchrotron radiation scan can be performed simultaneously in the area to be biopsied. After the patient 56 is in the appropriate position to perform the synchrotron radiation scan both the CT scan and synchrotron radiation scan can take place concurrently or in phases to identify and focus in on the area requiring biopsy. Further, during both the CT scan and synchrotron radiation scan the patient can be moved and/or rotated on the bed 94 to allow for correlating the image and providing at least a 2-D image where the synchrotron radiation scan provides a histologic (microscopic) slice thickness of the area of interest resulting in a radiographic biopsy. If the patient is rotated on the bed 94 it will be necessary to include stabilizing means to hold the patient in place.

Figure 5:
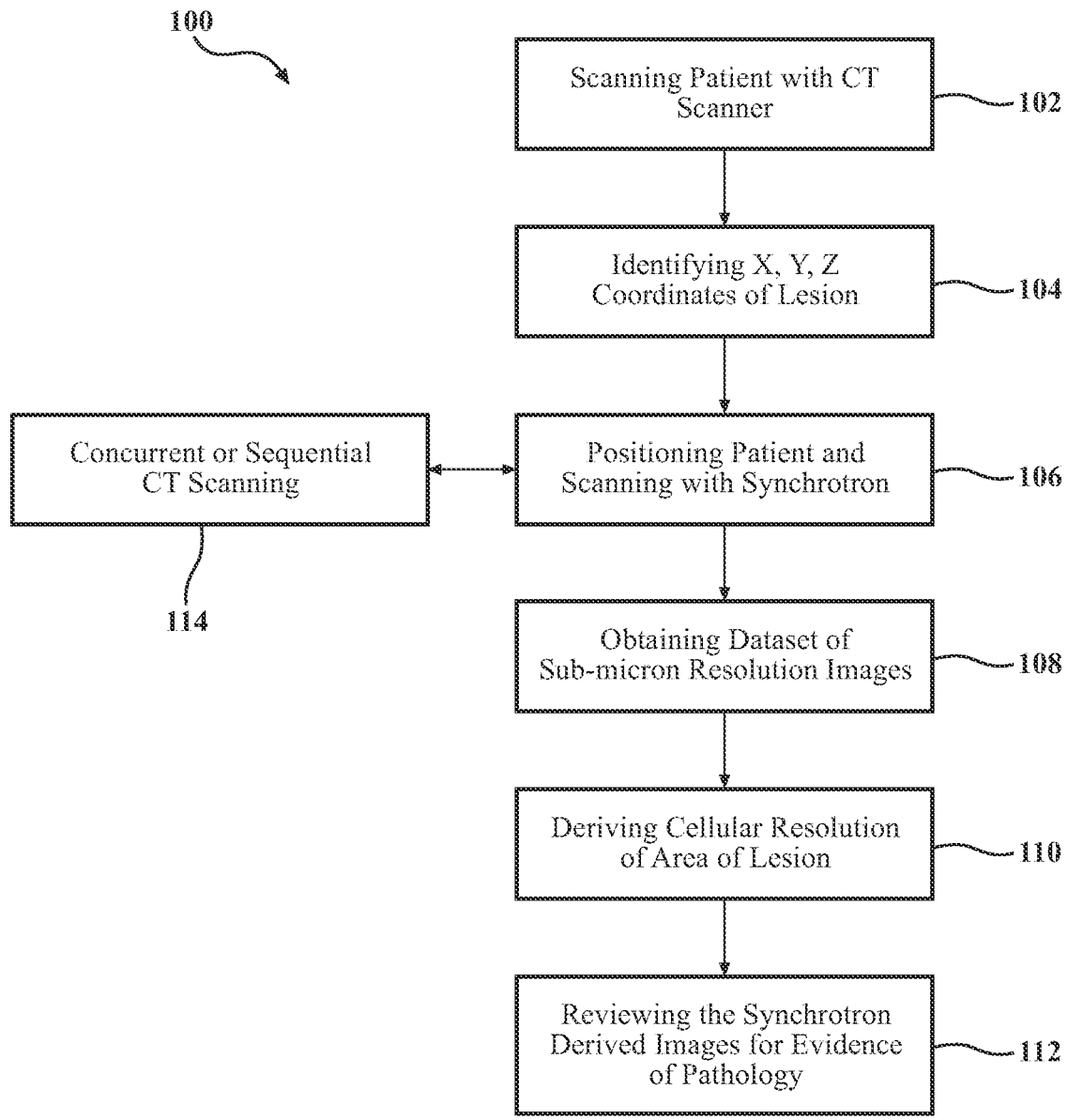
FIG. 5 is a flowchart of a first embodiment of a method of the invention.

With reference to FIG. 5, a nonlimiting embodiment of the method of the invention 100 begins with scanning a patient 102, a living human subject, with a CT scanning system. Any of the described CT scanning systems (refer to FIGS. 1-4) are suitable for this step. The next step 104 includes identifying with the CT scan an area of interest for biopsy such as a potential lesion and determining the X, Y and Z coordinates of the area of interest. Next, in step 106, positioning the patent, if necessary, for a synchrotron scan and performing a synchrotron scan. The next step 108 includes, obtaining a dataset of micron or sub-micron resolution images from the scanning with the synchrotron radiation source. The data is developed from the synchrotron scan. The next step 110 includes, computer enabled resolving of the dataset to derive cellular or subcellular level resolution of at least a portion of the area of potential pathology. The last step 112 includes, reviewing the images for evidence of pathology. Following these steps provides a radiologic biopsy of the patient.

In a nonlimiting embodiment, the method 100 further includes the step 114 of concurrent or sequential scanning with the CT scanner and the synchrotron scan. As already described in reference to FIGS. 2-4, certain embodiments of the radiologic biopsy system allow for concurrent CT scanning and synchrotron scanning. In this embodiment, the patient is positioned such that both the CT scan and the synchrotron scan can be focused on approximately the same X, Y, and Z coordinates of the patient where the potential lesion or other area of interest is located. A benefit of this arrangement is the ability to adjust the position of the patient while reviewing scout images from the CT scan in real-time to allow for more precise positioning of the patient for the synchrotron scan of the area of interest.

Figure 6:
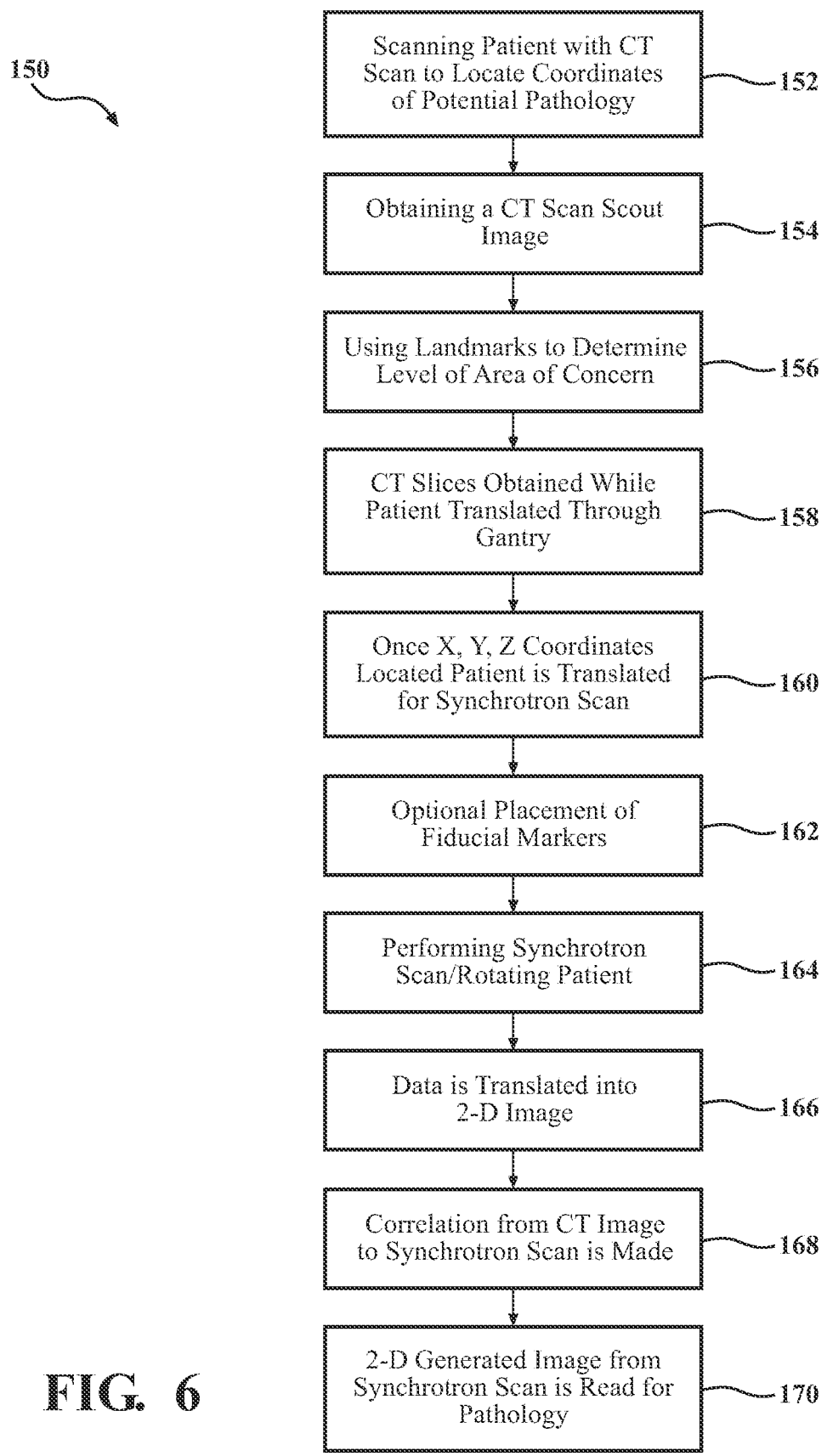
FIG. 6 is a flowchart of a second embodiment of the method of the invention.

Referring to FIG. 6, a second nonlimiting embodiment, the steps of a method of performing a radiological biopsy 150 of the invention includes a first step 152 of scanning a living human subject with a CT scan to locate the coordinates of an area of potential pathology and then using the coordinates to direct synchrotron radiation to obtain a high-resolution image of the area of potential pathology. This begins at step 154 with obtaining a CT scan scout image. Next, in step 156, from the scout image, a few key landmarks are used to roughly determine what level the area of concern is located and what area to scan. A subsection is blocked off for slice acquisition. Next, in step 158 using conventional CT, a number of slices are obtained while the patient table is translated through the gantry in a craniocaudal manner. The ideal slice position is selected which displays the desired location to biopsy and the table is moved to that position. The remaining locations of the lesion can be determined from the image itself. In step 160, once the X, Y, Z coordinates are determined by conventional CT scan, the patient is translated so that the lesion may be aligned with the synchrotron beam and permit scanning by synchrotron radiation. In step 162, in order to ensure that the level in question is directly aligned with the synchrotron beam, fiducial markers can be placed above and below the synchrotron aperture as the beam enters the inner part of the conventional CT gantry to ensure that it is in line with the desired level of scanning. Next, in step 164, once directly in the path of the synchrotron beam, the patient is rotated 180-360 degrees and a synchrotron-based image of the lesion in question is obtained. In the case of the horizontal method as described above in reference to FIGS. 4A and 4B, supports must be used to prevent the patient from falling off the bed. During synchrotron scanning, multiple projections are obtained while the specimen is rotated 180-360 degrees.

Next, in step 166 data from the synchrotron scan is translated into a 2-D image, with tomographic reconstruction performed using algorithms already in use with conventional CT and previously described above. In step 168, correlation from the conventional CT image to the slice obtained via synchrotron is made to determine the location of the lesion in question using methods already described. In step 170, the 2-D generated images from the synchrotron scan are read for potential pathology.

Figure 7:
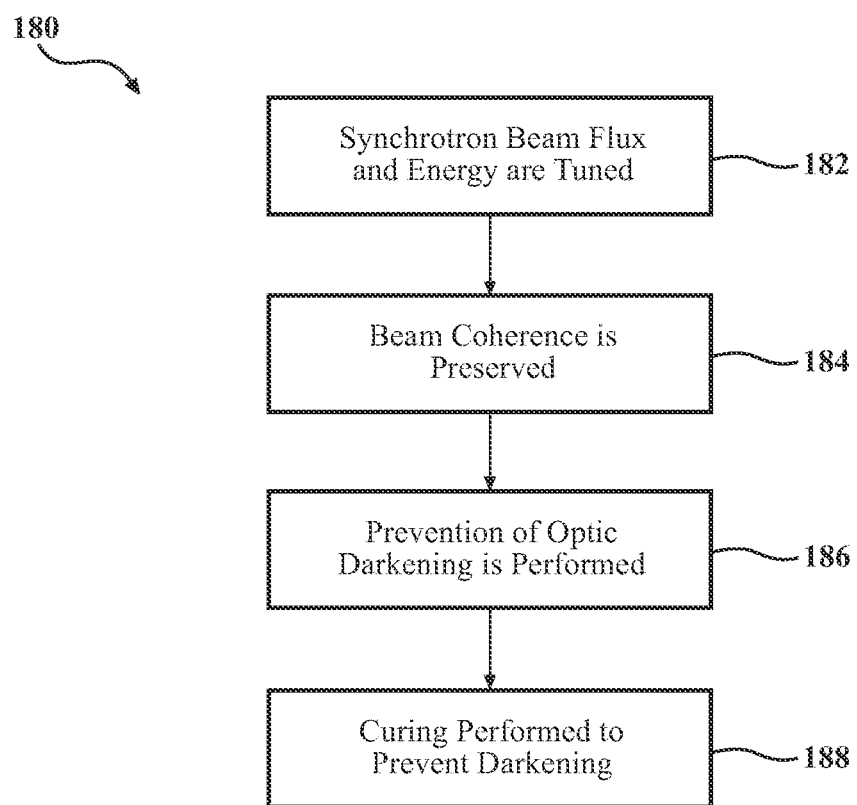
FIG. 7 is a flowchart of a third embodiment of the method of the invention.

Referring to FIG. 7, in a nonlimiting embodiment a method of the invention includes steps for preparing to perform and performing the synchrotron scan 180. At step 182, the synchrotron beam flux and energy are tuned prior to the procedure to ensure optimal average energy sufficient to penetrate through the patient but low enough to allow more rapid scans. Tuning can be achieved using filters such as molybdenum and copper filters for energy tuning. Fused silica bar attenuators allow for adjusting the beam flux and profile. Next, at step 184, prior to the procedure, beam coherence is preserved using filters and optics. Filters and optics are made of high-quality mirror polished materials. Optics can be made of pf6/IF1 beryllium for example. Scintillators are selected to be as dense as possible while not degrading resolution. At step 186, prevention of optics darkening is performed during scanning. Photodarkening can be prevented by intrinsic hardening by X-rays. Alternatively, darkening can be reduced through the use of a thin glassy carbon mirror to reduce internal scattering and lead glass in the front of an optic to stop as much scattering as possible. A beam stop can be used to prevent beam back scatter during scanning. In the case of a synchrotron, it can be made of a hollow tungsten cylinder. It is typically placed inside the flight tube just before the big Kapton window. In step, 188 following scanning, curing can be performed to ensure optics recovery, in the event of optics darkening.

The invention has been shown and described in what is considered nonlimiting embodiments. It is recognized that departures may be made within the scope of the invention and that modifications will occur to a person skilled in the art. With respect to the above description then, it is to be realized that the optimum dimensional relationships for the parts of the invention, to include variations in size, materials, shape, form, function and manner of operation, assembly, and use, are deemed readily apparent and obvious to one skilled in the art, and all equivalent relationships to those illustrated in the drawings and described in the specification are intended to be encompassed by the present invention.

The invention has been described in an illustrative manner. It is to be understood that the terminology, which has been used, is intended to be in the nature of words of description rather than of limitation. Many modifications and variations of the invention are possible in light of the above teachings. Therefore, within the scope of the appended claims, the invention may be practiced other than as specifically described.

What is claimed is:

1. A method of performing a radiologic biopsy, comprising:
   scanning a living human subject with a CT scanner and obtaining CT scan images of the living human subject;
   identifying in the CT scan images a localized area of potential pathology;
   identifying with the CT scanner an X, Y and Z coordinates within said area of potential pathology;
   scanning with a synchrotron radiation said area of potential pathology at, or proximate to said X, Y and Z coordinates;

obtaining a dataset of sub-micron resolution image data from said scanning with said synchrotron radiation; and resolving of said dataset to produce a radiographic image having cellular level resolution of at least a portion of said area of potential pathology.

2. The method of performing a radiologic biopsy of claim 1, further comprising:
algorithmically reducing motion artifact during said scanning with said synchrotron radiation.

3. The method of performing a radiologic biopsy of claim 1, further comprising:
repositioning the living human subject before the step of scanning with said synchrotron radiation to line up the X, Y and Z coordinates of said area of potential pathology with a beam of said synchrotron radiation.

4. The method of performing a radiologic biopsy of claim 1, further comprising:
during the step of scanning with said synchrotron radiation, rotating the living human subject.

5. The method of performing a radiologic biopsy of claim 1, wherein the steps of scanning the living human subject with a CT scanner and scanning with said synchrotron radiation are at least in part performed concurrently.

6. The method of performing a radiologic biopsy of claim 1, wherein said radiographic image is of comparable quality to a histologic slice of at least a portion of said area of potential pathology.

7. The method of performing a radiologic biopsy of claim 1, further comprising:
tuning a synchrotron beam flux and energy from said synchrotron radiation prior to the step of scanning with said synchrotron radiation to ensure that the average energy is sufficient to penetrate through the living human subject but low enough to allow fast scans.

8. The method of performing a radiologic biopsy of claim 1, wherein the CT scanner is a C-Arm CT scanner, wherein said C-Arm CT scanner includes an unobstructed pathway for allowing a synchrotron radiation beam from said synchrotron radiation to traverse said unobstructed pathway, wherein a direction of said synchrotron radiation beam and a direction of said scanning of said CT scanner are orthogonal.

9. The method of performing a radiologic biopsy of claim 8, wherein the steps of scanning the living human subject with a CT scanner and scanning with said synchrotron radiation are at least in part performed concurrently while said synchrotron radiation beam traverses said unobstructed pathway.

10. The method of performing a radiologic biopsy of claim 1, wherein the CT scanner is a horizontal CT scanner, wherein said horizontal CT scanner has an unobstructed pathway for allowing a synchrotron radiation beam from said synchrotron radiation to traverse said unobstructed pathway.

11. The method of performing a radiologic biopsy of claim 1, wherein the CT scanner is a horizontal CT scanner, wherein the living human subject is supported on a horizontal stage, wherein the horizontal stage is movable in an X, Y and Z direction, wherein the horizontal stage is adapted to rotate in a rotisserie-type manner around an axis perpendicular to a plane of the horizontal CT scanner.

12. The method of performing a radiologic biopsy of claim 1 further comprising:
reviewing said radiographic image for evidence of pathology.

13. A method of performing a radiologic biopsy, comprising:
scanning a living human subject with a CT scanner and obtaining CT scan images of the living human subject;
identifying in the CT scan images a localized area of potential pathology and an X, Y and Z coordinates within said area of potential pathology;
scanning with a synchrotron radiation said area of potential pathology at, or proximate to said X, Y and Z coordinates;
obtaining a dataset of sub-micron resolution image data from said scanning with said synchrotron radiation; and
resolving of said dataset to produce a radiographic image having cellular level resolution of at least a portion of said area of potential pathology.

14. The method of performing a radiologic biopsy of claim 13, further comprising:
algorithmically reducing motion artifact during said scanning with said synchrotron radiation.

15. The method of performing a radiologic biopsy of claim 13, further comprising:
wherein said living human subject is on a movable stage; moving said stage while scanning with said synchrotron radiation.

16. The method of performing a radiologic biopsy of claim 15, wherein said movable stage is adapted to controllably move so as to reduce a potential of motion artifact.

17. The method of performing a radiologic biopsy of claim 13 further comprising:
reviewing said radiographic image for evidence of pathology.

18. A method of performing a radiologic biopsy, comprising:
positioning a living human subject on a controllably movable stage;
scanning the living human subject with a CT scanner and obtaining CT scan images of the living human subject;
identifying in the CT scan images a localized area of potential pathology and an X, Y and Z coordinates within said area of potential pathology;
at least one of moving said controllably movable stage and moving a synchrotron radiation beam source while scanning with a synchrotron radiation said area of potential pathology at, or proximate to said X, Y and Z coordinates;
obtaining a dataset of sub-micron resolution image data from said scanning with said synchrotron radiation; and
resolving of said dataset to produce a radiographic image having cellular level resolution of at least a portion of said area of potential pathology.

19. The method of performing a radiologic biopsy of claim 18, further comprising:
algorithmically reducing motion artifact during said scanning with said synchrotron radiation.

20. The method of performing a radiologic biopsy of claim 18 further comprising:
reviewing said radiographic image for evidence of pathology.

* * * * *